United States Patent [19]

Krstenansky et al.

[11] Patent Number: 5,192,745
[45] Date of Patent: Mar. 9, 1993

[54] CYCLIC ANTICOAGULANT PEPTIDES

[75] Inventors: John L. Krstenansky, Cincinnati; Simon J. T. Mao, Loveland, both of Ohio

[73] Assignee: Merrell Dow Pharmaceuticals Inc., Cincinnati, Ohio

[21] Appl. No.: 764,989

[22] Filed: Sep. 23, 1991

Related U.S. Application Data

[63] Continuation of Ser. No. 405,106, Sep. 8, 1989, abandoned, which is a continuation-in-part of Ser. No. 53,204, May 21, 1987, abandoned.

[51] Int. Cl.$^5$ ................ A61K 37/02; C07K 7/06; C07K 7/08
[52] U.S. Cl. .................................... 514/9; 514/11; 514/14; 514/15; 514/822; 530/327; 530/328; 530/317; 930/260
[58] Field of Search ............... 530/328, 327, 317; 514/9, 11, 15, 14, 822; 930/260

[56] References Cited

U.S. PATENT DOCUMENTS

| | | | |
|---|---|---|---|
| 4,654,302 | 3/1987 | Fritz et al. | 530/324 |
| 4,668,662 | 5/1987 | Tripier | 530/324 |
| 4,767,742 | 8/1988 | Dodt et al. | 514/12 |
| 4,791,100 | 12/1988 | Krammer et al. | 514/12 |

FOREIGN PATENT DOCUMENTS

| | | |
|---|---|---|
| 0158986 | 10/1985 | European Pat. Off. |
| 171024 | 2/1986 | European Pat. Off. |
| 0276014 | 7/1988 | European Pat. Off. |
| 0291981 | 11/1988 | European Pat. Off. |
| 0291982 | 11/1988 | European Pat. Off. |
| 0347376 | 12/1989 | European Pat. Off. |

OTHER PUBLICATIONS

Rudinger, Peptide Hormones, Parsons (ed.), U. Park Press, Baltimore, pp. 1–7, (1976).
Hruby, Life Sciences, vol. 31, pp. 189–199 (1982).
Krstenansky et al., Biochim Biophys Acta, vol. 957, pp. 53–59 (Nov. 1988).
Mao et al, "Rapid purification and revised amino-terminal sequence of Hirudin: A specific thrombin inhibitor of the bloodsucking leech," Analytical Biochemistry, 161, 514–518 (1978).
Harvey et al, "Cloning and expression of a DNA coding for the anticoagulant hirudin from the bloodsucking leech, Hirudo medicinalis," Proc. Natl. Acad. Sci, U.S.A., vol. 83, pp. 1084–1088, Feb. 1986.
Krstenansky, J. L., et al., Thrombosis Research 54, 319–325 (1989).
Cram, D. J., et al., Organic Chemistry, 2nd Edition, McGraw Hill, p. 609 (1964).
Owen, T. J., et al., J. Med. Chem., 31, 1009–1011 (1988).
Minar, E., et al., Klin Wochenschr Feb 15;63(4):190-1 (1985) [abstract of].
Markwardt, F., et al., Thromb. Haemostasis, 52(2), 160–3 (1984) [abstract of].
Markwardt, F. et al., Thromb Haemost Jun 28:47(3):226–9 (1982) [abstract of].
Markwardt, F., et al., Thromb Haemost Jun 28:49(3):235–7 (1983) [abstract of].
Sturzebecher, The Thrombin (R. Machovich, Ed.) vol. 1, 131–160, CRC Press, Boca Roton, Fla. (1984).
Mao, S. J. T., et al., Biochemistry 27, 8170–8173 (1988).
Maraganore, J. M., et al., J. Biol. Chem. 264(15), 8692–8697 (1989).
S. Bajusz, et al., Peptides 32, 473 (1984).
Chemical Abstracts 52:2122 abstracting F. Markwardt, Z. Physiol. Chem. 308, 147–56 (1957).
J. Dodt, et al., FEBS Letters (165(2), 180–84 (1984).
Y-J. Chang, FEBS Letters 164(2), 307–13 (1983).
Derwent Ab. 86–162807/26. W. German Patent Appln. No. 3445532, published Jun. 19, 1986. C. Plantorgan, inventor.
Derwent Ab. 86–162802/26. W. German Patent Appln. No. 3445517, published Jun. 19, 1986, Gen-Bio Tec Ges Gen, assignee.
J. Dodt, et al., Biol. Chem. Hoppe-Seyler 366, 379–385 (1985).
D. Bagdy, et al., Methods Enzymol., 45 (Proteolytic Enzymes, Pt. B), pp. 674–675 (1976).
M. J. P. Pilat et al., Federatin Proc. 45(6), 1494, 76th Ann. Meeting, ASBC (Jun. 8–12, 1986.
J. L. Krstenansky, et al., FEBS Lett. 211(1) 11–16 (1987).

*Primary Examiner*—Y. Christina Chan
*Attorney, Agent, or Firm*—Kenneth J. Collier

[57] ABSTRACT

This invention relates to cyclic peptide derivatives which are useful anticoagulant agents.

8 Claims, No Drawings

| 5,192,745

CYCLIC ANTICOAGULANT PEPTIDES

This is a continuation of application Ser. No. 07/405,106, filed Sep. 8, 1989, now abandoned, which is a continuation-in-part of application Ser. No. 07/503,204, filed May 21, 1987, now abandoned.

FIELD OF THE INVENTION

This invention relates to novel cyclic peptides which are useful anticoagulant agents.

BACKGROUND OF THE INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Proplylactic administration of anticoagulants is believed to prevent a recurrance of embolism in patients with rheumatic or arteriosclerotic heart disease and to prevent certain thromboembolic complications of surgery. Administration of anticoagulants has also been indicated in the treatment of coronary artery and cerebrovascular disease. Artrial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense and allergic reactions which commonly follow administration of any foreign protein of this size.

Applicants have discovered a specific region of hirudin that is responsible, at least in part, for its anticoagulant activity. This region has been chemically synthesized and certain of its cyclic analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation. The peptides of this invention possess significant anticoagulant activity and their unusual ability to bind only to the recognition site without binding to the cleavage site of thrombin may allow for a scientifically interesting and therapeutically significant adjunct to anticoagulant therapy.

SUMMARY OF THE INVENTION

This invention relates to derivatives of Hirudin having the structural formula 1:

$$X-A_1-A_2-A_3-A_4-A_5-N(R_1)-\overset{D}{\underset{\underset{Alk_1}{|}}{C}}-R \quad \overset{\begin{array}{c}CO-A_7-A_8-NR_1'\\ \end{array}}{\underset{\underset{Alk_2}{|}}{R'-\overset{L}{C}-CO-A_{10}-A_{11}-Y}}$$
$$Alk_1-B-Alk_2$$

wherein
X is an amino terminal residue selected from hydrogen, one or two alkyl groups of from 1 to 6 carbon atoms, one or two acyl groups of from 2 to 10 carbon atoms, carbobenzylloxy, and t-butyloxycarbonyl;

$A_1$ is a bond or is a peptide containing from 1 to 5 consecutive amino acids of Hirudin;

$A_2$ is an amino acid selected from the group consisting of Phe, SubPhe, β-(2-thienyl)alanine, β-(3-thienyl)alanine, β-(2-furanyl)alanine, β-(3-furyanyl)alanine, β-(2-pyridyl)alanine, β-(3-pyridyl)alanine, β-(4-pyridyl)alanine, β-(benzothien-2-yl)alanine, β-(benzothien-3-yl)alanine, β-(1-naphthyl)alanine, β-(2-naphthyl)alanine, Tyr, and Trp;

$A_3$ is Glu or Asp;

$A_4$ is Glu, Pro or Ala;

$A_5$ is Ile, Val, Leu, Nle, Thr, Phe, or Met;

$A_7$ is Glu, Asp, Ala, or Gln;

$A_8$ is Glu or Asp;

$A_{10}$ is a lipophilic amino acid selected from Tyr, Met, Cha, Trp, Phe, Leu, Nle, Ile, Val, His, and Pro; or is a dipeptide selected from, Cha-Gln, Leu-Gln, or a dipeptide containing at least one of the said lipophilic amino acids and a amino acid found in Hirudin;

$A_{11}$ is a bond or is a peptide fragment containing from one to five consecutive amino acids of Hirudin;

Y is a carboxy terminal residue selected from OH, $(C_1-C_6)$alkoxy, amino, mono- or di-$(C_1-C_4)$alkyl substituted amino, and benzylamino;

R, R', $R_1$, and $R_1'$ are each selected from a hydrogen, and $(C_1-C_4)$alkyl group;

B is selected from —S—, —S—S—, or —S—Alk$_3$—S—;

$Alk_1$, $Alk_2$, and $Alk_3$ are each selected from a $(C_1-C_8)$methylene group; and wherein "D" and "L" indicate that the stereochemistry of the indicated carbon of attachment of said $Alk_1$ and $Alk_2$ when said $Alk_1$ and $Alk_2$ correspond to the amio acid side chain of D-cysteine and L-cysteine, respectively, or a pharmaceutically acceptable salt thereof, as anticoagulant agents.

An aspect of the pepides of this invention is their use as a method of reducing blood coagulation in a patient in need thereof which comprises administering an anticoagulant effective dose of the aforementioned peptide derivatives.

DETAILED DESCRIPTION OF THE INVENTION

The following common abbreviations of the amino acids are used throughout this specification:
Gly—glycine
Ala—alanine
Val—valine
Leu—leucine
Ile—isoleucine
Pro—proline
Phe—phenylalanine
Trp—tryptophan Met—methoionine
Ser—serine
Thr—threonine
Cys—cysteine
Tyr—tyrosine
Asn—asparagine
Gln—glutamine
Asp—aspartic acid
Glu—glutaminc acid
Lys—lysine
Arg—arginine
His—histidine
Nle—norleucine
Hyp—hydroxyproline
3,4-dehydroPro—3,4-dehydroproline
Tyr(SO$_3$H)—tyrosine sulfate
Pgl—phenylglycine
NMePgl—N-methyl-phenylglycine
Sar—sarcocine (N-methylglycine)
pSubPhe—para substituted phenylalanine
SubPhe—substituted phenylalanine
DAla—D-alanine
Ac—acetyl
Suc—succinyl
pClPhe—para-chloro-phenylalanine
pNO$_2$Phe—para-nitro-phenylalanine
Pen—penicillamine ($\beta,\beta$-dimethylcysteine)
DCys—D-cysteine
Cha—$\beta$—cyclohexylalanine An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, secpentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl and succinyl. The term "a (C$_1$–C$_8$-)methylene or ethylene group" refers to a bivalent group derived from an acyclic or cyclic, saturated or unsaturated alkyl group of from 1 to 8 carbon atoms by conceptual removal of two hydrogen atoms from one of the carbon atoms or from two of the adjacent carbon atoms of the alkyl group. Examples of the (C$_1$–C$_8$)methylene or ethylene groups of this invention are methylene or methylidene (—CH$_2$—), ethylidene (CH$_3$CH<), 1-methylethylidene (CH$_3$C(CH$_3$)<), 1-methylpropylidene or secbutylidene (CH$_3$CH$_2$C(CH$_3$)<), 2,2-dimethylpropylidene or neopentylidene (CH$_3$C(CH$_3$)$_2$CH<), ethylene or dimethylene (—CH$_2$CH$_2$—), methylethylene (-CH$_2$CH(CH$_3$)—), ethylethylene (—CH$_2$CH(C$_2$H$_5$)—), ethenylene or vinylene (—CH=CH—), 1,1-ethenylidene (CH$_2$=C<), 1,1-cyclohexylidene (C$_6$H$_8$<), and 1,2-cyclopentylidene (C$_5$H$_8$<). A halogen group is a fluoro, chloro, bromo or iodo group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines mono- or di-substituted at the ortho, meta, or para position of the phenyl moiety with (C$_1$–C$_4$) alkyl, (C$_1$–C$_4$) alkoxy, halogen, or nitro groups or with a methylenedioxy group, $\beta$-(2-thienyl)alanine, $\beta$-(3-thienyl)alanine,$\beta$-(2-furanyl)alanine, $\beta$-(3-furanyl)alanine, $\beta$-(2-pyridyl)alanine, $\beta$-(3-pyridyl)alanine, $\beta$-(4-pyridyl)alanine, $\beta$-(benzothien-2-yl)alanine, $\beta$-(benzothien-3yl)alanine, $\beta$-(1-naphthyl)alanine, $\beta$-(2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids.

The term "lipophilic amino acid" includes Tyr, Tyr(-SO$_3$H), Phe, Leu, Nle, Ile, Val, His, or Pro.

The natural amino acids with the exception of glycine, contain a chiral carbon atom. Unless otherwise specifically indicated, the optically active amino acids, referred to herein, are of the L-configuration. For example any of the amino acids of the A$_1$ or A$_{10}$ group can be of the D- or L-configuration. As is customary, the structure of peptides written out herein is such that the amino terminal end is on the left side of the chain and the carboxy terminal end is on the right side of the chain.

The term "dimers" is intended to mean those peptides which result from the linking of two seperate linear peptides during the cyclization step either in a head to head or head to tail fashion. In the course of performing the desired internal cyclization via the "B" group, some of the linear peptide starting material will link with another linear peptide starting material rather then with itself. The resulting product is a "dimer" in the sense that it is made up of two of the linear starting peptides but is not a dimer in the sense that the molecular formula of the dimer is exactly two times the molecular formula of the monomer. A dimer of the peptide derivatives of this invention will have the structural formula:

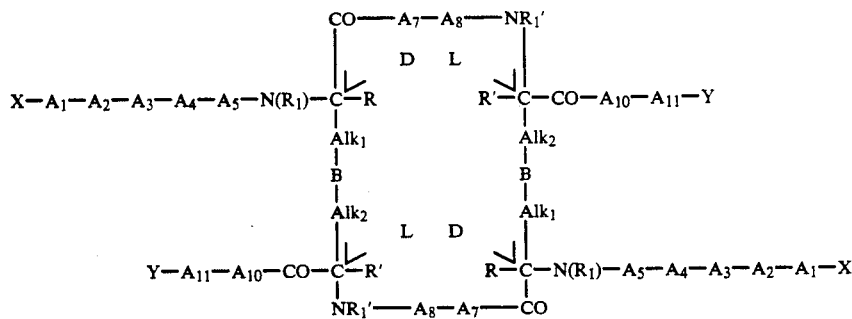

HEAD TO TAIL DIMER

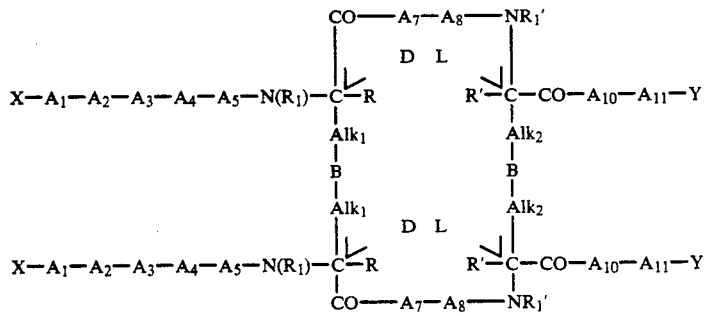

HEAD TO HEAD DIMER wherein the substituents are as defined above for structure 1. Throughout this disclosure, reference to the peptide derivatives includes the dimers and mixtures unless the context requires otherwise. While the mixtures of the monomer and dimer resulting from the cyclization step can be readily seperated by means well-known to those skilled in the art, the mixtures can be utilized in the antithrombotic compositions of this invention without separation.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein:

X is hydrogen, acetyl, or succinyl. Also preferred are those formula 1 compounds wherien
$A_1$ is
  -His-Asn-Asp-Gly-Asp-,
  -Asn-Asp-Gly-Asp-,
  -Asp-Gly-Asp-,
  -Gly-Asp-,
  -Asp-, or a bond.
$A_2$ is preferably Phe, $\beta$-(2-thienyl)alanine, $\beta$-(3-thienyl)alanine, Tyr, Trp, or pClPhe;
$A_3$, Glu;
$A_4$, Glu, Asp, Pro, or Ala;
$A_5$, Ile;
$A_7$, Glu, Asp, or Ala;
$A_8$, Glu or Asp;
$A_{10}$, Leu, Leu-Gln, or Cha-Gln;
$A_{11}$, Pro, Gln, Asp, Asp-Glu, or a bond;
$Alk_1$ and $Alk_2$, each a methylene group;
Y, OH or $NH_2$; and
B, —S—S—.

Especially preferred are those peptide derivatives of formula 1 wherein either
  X is acetyl or succinyl and
  $A_1$ is Gly-Asp, Asp, or a bond;
  $A_2$, is Phe, $\beta$-(2-thienyl)alanine, or Tyr;
  $A_3$, Glu;
  $A_4$, Glu or Pro;
  $A_5$, Ile;
  $A_7$, Glu;
  $A_8$, Glu or Asp;
  $A_{10}$, -Leu-Gln-, Cha-Gln, or -Asp-Glu;
  $A_{11}$, Pro, Gln, Asp, Asp-Glu, or a bond;
  R, R', $R_1$, and $R_1'$, each hydrogen;
  $Alk_1$ and $Alk_2$, each a methylene group;
  B, —S—S—; and
  Y, OH or $NH_2$.

The peptides of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., Chem. Ind. (London) 38, 1597-98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1-6. The protected amino acid can be bound to the resin by the procedure of Gisin, Helv. Chem Acta, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzylcarbonyl, p-bromobenzyloxycarbonyl, p-methoxybenzyloxycarbonyl, 1-(p-biphenylyl)-1-methylethoxycarbonyl, α,α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, J. Pharm. Sci., 59, pp. 1-27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, Analyt. Biochem. 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxycarbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

In general, the cyclized peptides are prepared from an appropriate linear derivative either prior to or after removal of the linear peptide from the solid support. The compounds of structure 1 wherein B is a -S-S- group are prepared from the corresponding free sulfhydrylcontaining, linear peptides by well known oxidative coupling technics such as by oxidizing the linear peptide with potassium ferricyanide described in, for example, Stewart et al., "Solid Phase Peptide Synthesis" (Freeman & Co., San Francisco 1969), Chapter 1, p. 95. The compounds of Structure 1 wherein B is a -S-Alk$_3$-S- group and Alk$_3$ is a (C$_1$-C$_8$)ethylene group can be prepared from the free sulfhydryl-containing linear peptides by reaction with a 1,2-dibromo derivative of an appropriate acyclic or cyclic, saturated or unsaturated alkyl in a manner analogous to that described in H. I. Mosberg and J. R. Omnaas, *J. Amer. Chem. Soc.* 107, 2986–2987 (1985). The compounds of structure 1 wherein B is a -S-Alk$_3$-S- group and Alk$_3$ is a (C$_1$-C$_8$-)methylene group are prepared by reaction of the free sulfhydryl-containing linear peptide with an appropriate acyclic or cyclic, saturated or unsaturated alkyl ketone or aldehyde in a manner analogous to that described in *J. Amer. Chem. Soc.* 76, 1945 (1954). The preparation of those compounds of structure 1 wherein B is an -S- group can be accomplished in the manner set forth in K. Jost, *Collect. Czech. Chem. Commun.* 36, 218 (1971) and in U.S. Pat. No. 4,161,521.

An aspect of the peptides of this invention is their use as a method of reducing blood coagulation in a patient in need thereof which comprises administering an anticoagulant effective dose of the aforementioned peptide derivatives.

The anticoagulated effective does of a peptide derivative of this invention is from 0.2 mg/kg to 250 mg/kg of patient body weight per day depending on the patient, the severity of the thrombobotic condition to be treated and the peptide derivative selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containg a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of

H—Gly—Asp—Phe—Glu—Glu—Ile—DCys—Glu—Glu—Cys—Leu—Gln—OH

The peptide was snythesized by solid-phase methods using 0.1 mmol of a 0.66 mmol/g Boc-Gln-PAM resin. Double symmetrical anhydride couplings were performed with 2.0 mmol Nα-Boc-amino acid (Peptides International) except in the case of Boc-Gln, which was coupled by the DCC/HOBT method. The side chain protection utilized was: Asp(Chx), Cys(pMeBzl), Glu(Bzl). Upon completion of the synthesis the Nα-Boc protection was removed with 50% trifluoroacetic acid in methylene chloride. The resin was washed three times with methylene chloride, neutralized with three washings of 10% diisopropylethylamine in methylene chloride, washed three times with methylene chloride, acetylated with N-acetylimidazole in methylene chloride, washed three times with methylene chloride, and dried in vacuo. The peptide was deprotected and cleaved from the resin with water and the pH adjusted to 8.5 with ammonium hydroxide. Potassium ferricyanide (0.01N) was added to the solution until a yellow color persisted. The solution was stirred for 30 minutes, then the pH was adjusted to between 4 and 5 with acetic acid. The mixture was then stirred with "BIO-RAD" AG3-X4A ("BIO-RAD" is a Trademark of Bio-Rad Laboratories, Richmond, Calif.) ion exchange resin for 2 hours. The mixture was filtered and the filtrate lyophilized.

The peptide was purified by desalting on a 92×2.6 cm "SEPHADEX" G-15 ("SEPHADEX" is a Trademark of Pharmacia Incorporated, Piscataway, N.J.) column in 5% aqueous acetic acid and lyophilized. Preparative HPLC was performed on a $C^{18}$ "VYDAC" 218TP1010 ("VYDAC" is a Trademark of The Separations Group of Hesperia, Calif. 92345). (250×10 mm) column with acetonitrile in 0.1% aqueous trifluoroactic acid at 5 ml/min. The major peak was collected and lyophilized leaving the desired product. Homogeneity was determined by HPLC and TLC. HPLC "VYDAC" 218TP54 ("VYDAC" is a Trademark of The Separations Group of Hesperia, Calif. 92345) (250×4.6 mm) $C^{18}$ Column, 2 ml/min, $t_o$=1.8 min: time of elution with a 25-50% acetonitrile in 0.1% trifluoroacetic acid linear gradient at 1%/min. (HPLC) is 5.5 min. Fast Atom Bombardment—Mass Spectrophotometry (FAB-MS): (M+H)—1411.7±1 mµ (calcd. 1410). Amino acid analysis: (6N HCl hydrolysis; 24 hr. at 106° C.), see Table 1, 57% peptide content by weight.

In a similar manner, the peptide of the following structural analysis was prepared:

EXAMPLE 2

[Suc—Tyr—Glu—Glu—Ile—DCys—Glu—Glu—Cys—Cha—Gln—NH$_2$]

Analysis of the peptide was as follows: FAB-MS: (M+H)—1395.8; Amino acid analysis: (6N HCl hydrolysis; 24 hr. at 106° C.; see table 1, example 2).

We claim:

1. A peptide derivative of the formula $X-A_1-A_2-A_3-A_4-A_5-$

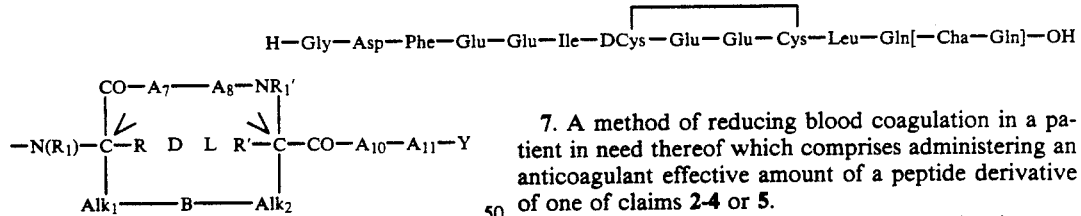

wherein
X is an amino terminal residue selected from hydrogen, one or two alkyl groups of from 1 to 6 carbon atoms, one or two acyl groups of from 2 to 10 carbon atoms, carbobenzylloxy, and t-butyloxycarbonyl;
$A_1$ is Gly-Asp, or a bond;
$A_2$ is Phe or Tyr;
$A_3$ is Glu;
$A_4$ is Glu;
$A_5$ is Ile;
$A_7$ is Glu;
$A_8$ is Glu;
$A_{10}$ is Leu;
$A_{11}$ is Gln;
Y is a carboxy terminal residue selected from OH, ($C_1$-$C_6$)alkoxy, amino, mono- or di-($C_1$-$C_4$)alkyl substituted amino, and benzylamino;
R, R', $R_1$, and $R_1'$ are each selected from a hydrogen, and ($C_1$-$C_4$)alkyl group;
B is -S-S-; and
$Alk_1$ and $Alk_2$ are each selected from a ($C_1$-$C_8$)methylene group; and wherein "D" and "L" indicate that the sterochemistry of the indicated carbon of attachment of said $Alk_1$ and $Alk_2$ when said $Alk_1$ and $Alk_2$ correspond to the amino acid side chains of D-cysteine and L-cysteine, respectively, or a pharmaceutically acceptable salt thereof.

2. A peptide derivative of claim 1 wherein X is H, acetyl, or succinyl.

3. A peptide derivative of claim 1 wherein Y is OH or NH$_2$.

4. A peptide derivative of claim 1 wherein R, R', $R_1$, $R_1'$ are each a hydrogen.

5. A peptide derivative of claim 1 wherein $Alk_1$ and $Alk_2$ are each a methylene group of the formula —(CH$_2$)—.

6. A peptide derivative of claim 1 which is

H—Gly—Asp—Phe—Glu—Glu—Ile—DCys—Glu—Glu—Cys—Leu—Gln[—Cha—Gln]—OH

7. A method of reducing blood coagulation in a patient in need thereof which comprises administering an anticoagulant effective amount of a peptide derivative of one of claims 2-4 or 5.

8. A method of reducing blood coagulation in a patient in need thereof which comprsies administering an anticoagulant effective amount of a pharmaceutically acceptable salt of a peptide derivative of claims 2-4 or 5.

* * * * *